United States Patent
Suwalski

(10) Patent No.: US 12,343,058 B2
(45) Date of Patent: Jul. 1, 2025

(54) CRYOPROBE FOR MINIMALLY INVASIVE CARDIAC ABLATION WITH A FUNCTIONAL TIP

(71) Applicant: Medinice S. A., Warsaw (PL)

(72) Inventor: Piotr Suwalski, Warsaw (PL)

(73) Assignee: Medinice S. A., Warsaw (PL)

(*) Notice: Subject to any disclaimer, the term of this patent is extended or adjusted under 35 U.S.C. 154(b) by 549 days.

(21) Appl. No.: 17/865,531

(22) Filed: Jul. 15, 2022

(65) Prior Publication Data

US 2023/0065381 A1 Mar. 2, 2023

(30) Foreign Application Priority Data

Aug. 31, 2021 (EP) ..................................... 21461581

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00389* (2013.01); *A61B 2017/00398* (2013.01); *A61B 2018/00351* (2013.01); *A61B 2018/00577* (2013.01); *A61B 2018/00696* (2013.01); *A61B 2018/0212* (2013.01)

(58) Field of Classification Search
CPC .......... A61B 18/02; A61B 2017/00389; A61B 2017/00398; A61B 2018/00351; A61B 2018/00577; A61B 2018/00696; A61B 2018/0212; A61B 2018/00041; A61B 2018/00791
See application file for complete search history.

(56) References Cited

U.S. PATENT DOCUMENTS

2009/0124972 A1* 5/2009 Fischer ................. A61B 18/02
604/113
2011/0087205 A1 4/2011 Christian et al.
(Continued)

FOREIGN PATENT DOCUMENTS

CN 209253102 U 8/2019

*Primary Examiner* — Ankit D Tejani
*Assistant Examiner* — Joshua Brendon Solomon
(74) *Attorney, Agent, or Firm* — Dickinson Wright PLLC; Andrew D. Dorisio

(57) ABSTRACT

A cryoprobe for minimally invasive cardiac ablation with a functional tip (2) according to the invention comprises a handle (5) and a first tip (1), having a cooling system for destroying tissues by freezing them, and at least one functional tip (2). Wherein the functional tip (2) is movable relative to the first tip (1), and it has at its end (4) at least a temperature measuring system (6) for the tissues being destroyed by the first tip (1). The first tip (1) is in turn mounted in a handle (5) provided with at least one button (3) for controlling the functional tip (2). Both the first tip (1) and at least one functional tip (2) have a part susceptible to a plastic change in shape. The cryoprobe according to the invention is characterised in that at least one functional tip (2) has a central part susceptible to a plastic change in shape, and a rigid part at its end, and the first tip (1) has a part susceptible to a plastic change in shape at its end, and the remaining part of the first tip (1) is rigid.

The invention also comprises a method for controlling the cryoprobe.

14 Claims, 3 Drawing Sheets

(56) References Cited

U.S. PATENT DOCUMENTS

2014/0012155 A1* 1/2014 Flaherty .............. A61B 5/4233
              600/549
2014/0200567 A1  7/2014 Cox et al.
2020/0000511 A1  1/2020 Morejohn et al.

* cited by examiner

CRYOPROBE FOR MINIMALLY INVASIVE CARDIAC ABLATION WITH A FUNCTIONAL TIP

This application claims priority to European Patent Application No. EP21461581.7 filed on Aug. 31, 2021, the disclosure of which is hereby incorporated by reference.

FIELD OF THE INVENTION

The object of the invention is a cryoprobe for minimally invasive cardiac ablation with a functional tip, for controlling the parameters of the ablation at the outer side of the tissue.

PRIOR ART

The document US20110087205A1 and the document US20140200567A1 disclose a system, a device and a method for the ablation of target tissues neighbouring the pulmonary veins of a patient by cutting. The ablation device has a hinge comprising a cam assembly, a movable arm, a movable jaw and a lower jaw. Control of the jaws is performed by means of handles held with one hand. The jaws are equipped with sensors and elements for transferring the energy needed for tissue ablation. The tools described in the documents have rigid working tips and rigid jaws, which cannot be shaped and adjusted to a shape desired during surgery. This reduces the precision of temperature measurement and extends the area of the ablation process, which is unpreferable for the neighbouring tissue.

The document US20200000511A1 discloses a cryoprobe for cardiac ablation, which comprises a handle, a control button and two tips, one of which is movable in relation to the other one. The tips have a rigid part and a flexible part capable of matching the shape of the tissue. The tips disclosed in the document have a predetermined shape; they are flexible and rotary. Ablation is performed simultaneously on both sides of heart tissue, in order to shorten the time of the procedure. The tool described in the document does not have a sensor, and it does not measure the temperature of the tissue. During ablation, more cells undergo freezing than it is required.

The document CN209253102U discloses a solution similar to those disclosed in the already discussed documents. Wherein it comprises a cryoprobe for cardiac ablation, which has two rigid tips, one of which is a cooling tip introduced inside the tissue, and the other one is a measuring tip applied to the outside of the tissue. Due to the fact that the tips are rigid, it is impossible to shape them during the procedure. This results in freezing unnecessary parts of the tissues or in making additional cuts in the tissue in a case when reaching the required place of ablation is hindered. This makes ablation performed by this device highly invasive.

The object of the present invention is a cryoprobe without the abovementioned drawbacks, for performing precise ablations in the shortest time possible in order to reduce damage to tissues not undergoing ablation.

SUMMARY OF THE INVENTION

Therefore, it is the purpose of the present invention to provide a cryoprobe which allows to shorten the time of performing the procedure. A cryoprobe for minimally invasive cardiac ablation with a functional tip according to the invention comprises a handle and a first tip having a cooling system for destroying tissues by freezing them, and at least one functional tip. Wherein the functional tip is movable relative to the first tip, and it has at its end at least a temperature measuring system for the tissues being destroyed by the first tip. The first tip is mounted in the handle equipped with at least one button for controlling the functional tip. Both the first tip and at least one functional tip have a part susceptible to a plastic change in shape. The cryoprobe according to the invention is characterised in that at least one functional tip has a central part susceptible to a plastic change in shape, and a rigid part at its end, and the first tip has a part susceptible to a plastic change in shape at its end and the remaining part of the first tip is rigid.

Preferably, the functional tip is hingedly attached to the first tip.

Preferably, the functional tip is permanently attached by an elastic element to the first tip.

Preferably, the functional tip is configured and adjusted to provide control by means of a button, using a lever mechanism.

Preferably, the functional tip is configured and adjusted to provide control by means of a button, using a rotary mechanism.

Preferably, the functional tip is configured and adjusted to provide control by means of a button, using a tensioning mechanism.

Preferably, the functional tip is configured and adjusted to provide control by means of a button, using electric actuators.

Preferably, the functional tip is configured and adjusted to provide control by means of a button, using pneumatic actuators.

Preferably, it has a controller for automatic or semi-automatic control of the movement of the functional tip.

Preferably, it has an elastic element for pressing the functional tip in a direction towards the first tip.

Preferably, the first tip has a system for heating the surface of the first tip, for shortening the time of unfreezing the first tip from the frozen tissue.

Preferably, the temperature measuring system for the tissue comprises a thermocouple and/or a semiconductor sensor.

The invention also comprises a method for controlling the cryoprobe, characterised by comprising the following steps:
 a) Placing the previously shaped first tip in the inner part of the tissue;
 b) Activation of the system for destroying tissues for a predetermined time needed to destroy tissues of given thickness;
 c) Applying the end of the previously shaped movable tip to the place where the first tip is destroying the tissues;
 d) Measurement of the physical quantities of the tissues being destroyed;
 e) Detecting the exceeded critical values of physical quantities which indicate the destruction of tissues;
 f) Distancing the end from the place of tissue destruction;
 g) Deactivating the system for destroying tissues;
 h) Removing the first tip from the inner part of the tissue;

Preferably, it uses a cryoprobe having a controller for automatic or semi-automatic control of the movement of the functional tip, while step f) and/or g) is performed automatically.

BRIEF DESCRIPTION OF THE FIGURES

The invention will now be presented in a preferable embodiment, with reference to the attached drawings, in which.

DETAILED DESCRIPTION

In a Preferable Embodiment

Figure 1:
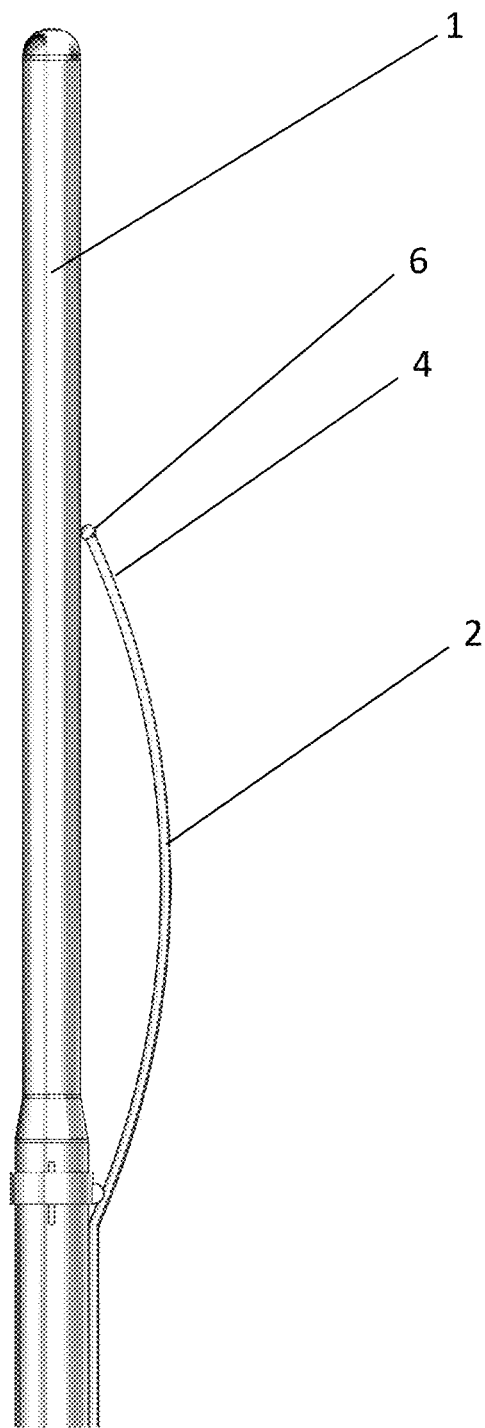
FIG. 1 Presents a side view of the tips of the cryoprobe.
Figure 2:
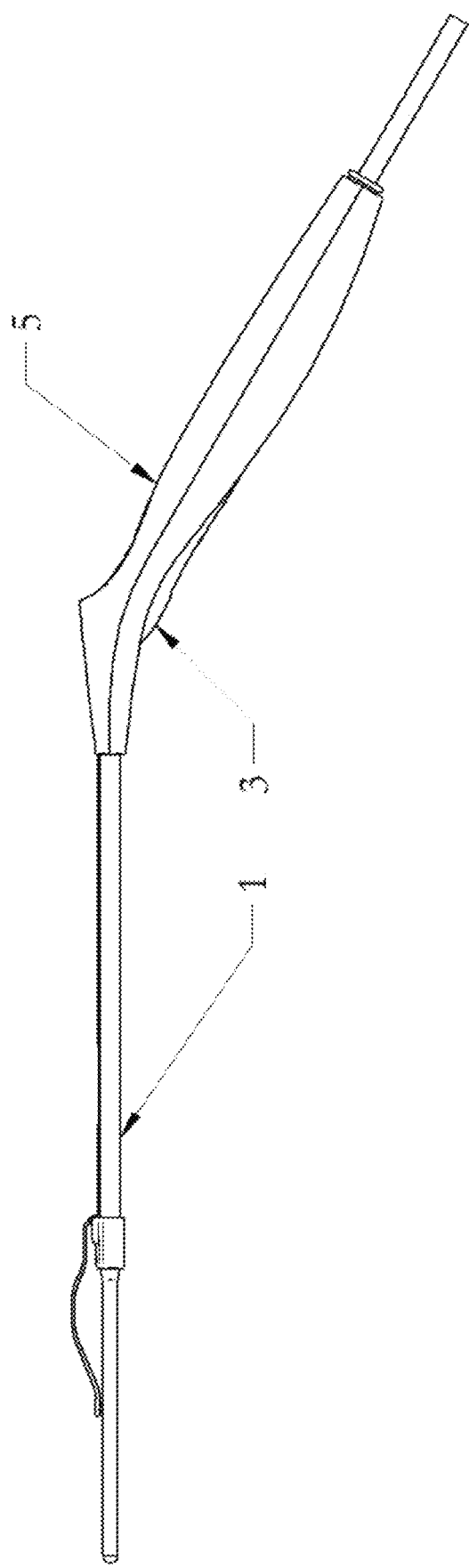
FIG. 2 Presents an isometric view of the cryoprobe.
Figure 3:
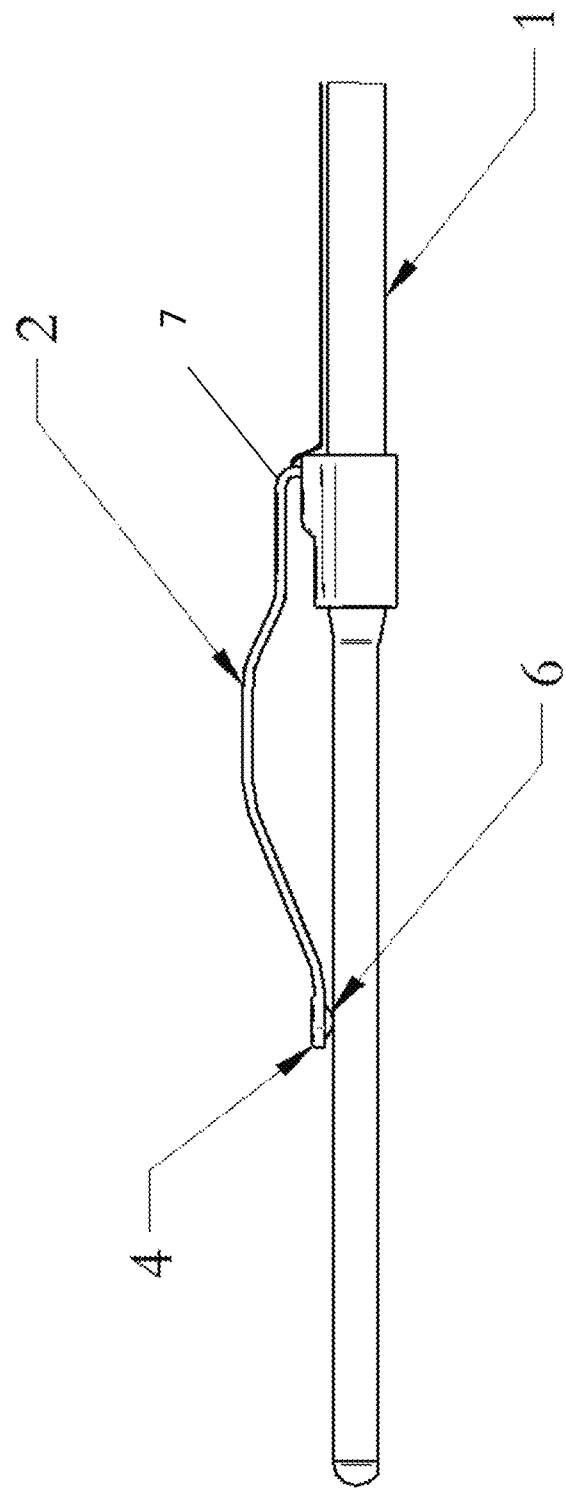
FIG. 3 Presents a schematic view of the mechanism pressing the functional tip 2 by means of the elastic element 7.

In cryoablation, negative temperatures are used to precisely neutralise the fragments of tissues responsible for faulty conduction of electrical pulses in the heart. Ablation using cold has the widest use in eliminating the cause of atrial fibrillation. In order to kill the cells, the tissue temperature should drop below −40 degrees Celsius. In this therapy, the effectiveness of cryoablation reaches even 80 percent.

Cryoablation is effective if the heart tissue is thoroughly frozen. If the wall of the heart is not thoroughly frozen and no permanent cell necrosis is caused, electrical conductivity bridge may form in the cells, and instead of eliminating atrial fibrillation, they can further intensify it. In order to eliminate the uncertainty related to the fact whether the wall of the heart has been thoroughly frozen, a need to design an active measurement of temperature simultaneously on both sides of the frozen tissue has been noticed.

During the cryoablation procedure, a very important element is the measurement of pericardium temperature during the procedure. Temperature measurement only at the cryoprobe may not be sufficient, e.g.: due to the insufficient contact of the cryoprobe with the heart tissue. In the event of insufficient contact, the temperature measured at the cryoprobe may be sufficient to kill the cells, while the temperature on the outer side of the heart may not drop below the cell death temperature, and it would not cause their necrosis.

In a preferable embodiment, the device consists of a cryoprobe having a handle 5 with a first tip 1 having a cooling system for the destruction of tissues by freezing them. This system uses the energy of liquid gas flowing inside the tip 1, preferably nitrogen, helium, hydrogen. In addition, the cryoprobe has a movable functional tip 2, the movable functional tip 2 being movable relative to the tip 1. At its end 4, it has a temperature measuring system 6 in the form of a thermometer. The tip 2 is attached pivotally and hingedly to the tip 1, which has handles 5 with buttons 3 for controlling the cooling and the movable tip 2. The temperature measuring system 6 performs the measurement of physical quantities, based on which the tissue temperature is determined. Depending on the adopted temperature measurement method, the following measurements are used: of electric voltage at the contact of two different metals, a change in the resistance of an element, a change in the parameters of the semiconductor connector, of thermal radiation parameters of the body, e.g. a pyrometer, a change in colour—a visual thermometer.

In a preferable embodiment, the temperature measuring system 6 consists of a thermocouple, e.g. type K. The system 6 measures the voltage of the thermocouple connector. The type K thermocouple receives connector voltage of approx. 16.5 mV for living tissue with a temperature of approx. 36 C and approx. −20 mV for a temperature of −80 C, assumed in the embodiment as the ablation temperature of the tissue. Other types of thermocouples may be applicable, wherein their voltage and temperature characteristics may be different and may depend on the type of the connector, its composition and dimensions.

In another preferable embodiment, a thermistor is used as the system 6, meaning a resistor with variable resistance and temperature characteristics. The measured physical quantity is resistance. The resistances of thermistors for various temperatures are standardised. For an ablation temperature of −80 C in a preferable embodiment, the resistance of a Pt100 platinum thermistor is 68.33Ω, and for a living tissue temperature of 36 C, this resistance is approximately 112Ω.

In another embodiment, a semiconductor thermometer is used as the system 6, preferably the system with a Zener diode. The measured quantity is the diode breakdown voltage, which is proportional to the temperature of the connector by approximately 10 mV/K, and in a preferable embodiment for a temperature of 25 C it is −3.4V. There are known Zener diodes with different values of breakdown voltage within a range from 1.2 to 200V, and with different proportions of the connector temperature to the value of breakdown voltage.

An alternative embodiment uses the measurement of tissue radiation energy by means of a graduated optic system and a detector. The measurement uses a close infrared detector within a 800-1200 nm wavelength range.

Both tips have a part susceptible to a plastic change in shape. Knowing the shape of the tissue undergoing ablation, an operator may shape the plastic parts of the tips as needed. The tip 1 is shaped at its end in order to duplicate the inner shape of the tissue being frozen. The tip 1 at its plastic end is made of a material susceptible to plastic deformation, preferably an alloy of aluminium or copper. In another preferable embodiment, the plastic end of the tip 1 is made of a material difficult to deform plastically, e.g. steel, but properly weakened, e.g. by a series of cuts, or shaped in the form of a spring, a thin mantle, a ribbon folded into the form of a tube, or elastic bellows. The functional tip 2 in its central part is shaped such that its central part circumvents the outer part of the tissue not undergoing ablation, and possible obstacles along the way to the place of ablation, and simultaneously in order to provide mechanical contact of the rigid end 4 of the functional tip 2 with the tissue undergoing ablation from its outer side. Such separable and different shaping of the tips allows for a certain mechanical contact of the end of the tip 1 with the tissue being frozen from the inside, which increases the precision of ablation and maximises the transfer of energy to the frozen tissue. At the same time, it provides a certain contact of the end 4 of the functional tip 2 precisely with the place of freezing the tissue, and a precise measurement of this tissue. Such shaping of the functional tip 2 allows for its minimal contact with the tissue, and a discrete measurement of temperature. Due to the fact that the tip does not touch the tissues not undergoing ablation, which have a considerably higher temperature, the measurement is more precise and faster.

Because of this, the process of freezing the tissues can be finished quicker than in a case when the measurement is performed with a rigid arm contacting the tissue undergoing ablation and not undergoing ablation.

The quickness and precision of measurement allow to shorten the time of cooling down the tissues and propagation of low temperature beyond the area of ablation, to places where it is not necessary to destroy the tissues. Shortening the time of the procedure is preferable for tissues not undergoing ablation.

The functional tip 2 is plastic and it can be placed in any position relative to the freezing part—of the tip 1 of the cryoprobe. Plastic means capable of changing its shape and retaining this shape.

In a preferable embodiment, the elastic element 7, e.g. a metal spring, is placed in the mechanism, and it presses the measuring tip against the tissue with a constant force.

In another preferable embodiment, the functional tip 2 is attached by means of the elastic element instead of a hinge.

The control of the functional tip 2 is realised by means of lever, rotary or tensioning mechanisms. In another preferable embodiment, it can be controlled by means of electrical actuators, e.g. electrical motors or electromagnets, or by means of pneumatic actuators, e.g. pneumatic cylinders.

The functional tip and the ablation process are controlled manually using the buttons 3, or automatically. In the case of manual control, the operator must know the thickness and type of the tissue undergoing ablation, and determine or calculate the time necessary to perform the ablation, meaning to cool down a certain volume of cells to an adequately low temperature by a cooling agent with an adequately low temperature. Calculations of this type are known to the people performing ablations.

In a preferable embodiment, the cryoprobe has an additional system heating the freezing part of the tip 1. Upon completing the ablation, the tip 1 may freeze to the tissue and its removal will be impossible, or an attempt to remove it will damage the tissues frozen to it. The heating element activated at the moment when the operator finishes the ablation will heat up the surface of the tip 1, and it will unfreeze it from the tissue, which will allow the safe removal of the tool.

In a preferable embodiment, the cryoprobe has a controller, by means of which the movement of the activators of the functional tip 2 is controlled. The control may proceed automatically or semi-automatically. The semi-automatic action is such that an operator draws the functional tip 2 towards the tissue, and the automatic system activates the distancing mechanism.

The automatic action, meaning one in which the controller performs the drawing and distancing, is such that after the start of the ablation process, the controller measures its time, and at a predetermined or calculated time, upon the passing of which the tissue is expected to be close to be thoroughly frozen, it draws the functional tip 2 to the place of freezing, it performs the measurement and waits for the desired temperature to be reached. Once the desired temperature of the tissue has been reached—the controller distances the functional tip 2. In an alternative embodiment, cooling is deactivated after distancing the functional tip 2, followed by activation of the heating of the cooling tip 1. The cooling tip 1 heats up faster than the frozen tissue, due to which it unfreezes safely and the tool is ready to be removed from the tissue. In addition, the automatic action shortens the time of ablation, but it requires entering data about the tissue being frozen and the type of the cooling agent.

The parameters of ablation, performed both manually and automatically, are set up before the procedure by people skilled in the art, using known empirical and mathematical models as well as experimental data.

Preferable embodiments refer to the ablation of the cardiac muscle tissue. Alternatively preferably, they can be other tissues or cell groups.

The invention claimed is:

1. A cryoprobe for minimally invasive cardiac ablation with a functional tip, comprising a handle (5) and
a first tip (1) having a cooling system for destroying tissues by freezing them
and at least one functional tip (2),
the functional tip (2) being movable relative to the first tip (1) and having at its end (4) at least a temperature measuring system (6) for the tissues being destroyed by the first tip (1), while the first tip (1) is mounted in the handle (5) equipped with at least one button (3) for controlling the functional tip (2), both the first tip (1) and the functional tip (2) having a part susceptible to a plastic change in shape, characterized in that the functional tip (2) has a central part susceptible to a plastic change in shape and a rigid part at its end, and the first tip (1) has a part susceptible to a plastic change in shape at its end, and the remaining part of the first tip (1) is rigid.

2. The cryoprobe according to claim 1, characterized in that the functional tip (2) is hingedly attached to the first tip (1).

3. The cryoprobe according to claim 1, characterized in that the functional tip (2) is permanently attached by an elastic element (7) to the first tip (1).

4. The cryoprobe according to claim 1, characterized in that the functional tip (2) is configured and adjusted to provide control by means of the button (3), using a lever mechanism.

5. The cryoprobe according to claim 1, characterized in that the functional tip (2) is configured and adjusted to provide control by means of the button (3), using a rotary mechanism.

6. The cryoprobe according to claim 1, characterized in that the functional tip (2) is configured and adjusted to provide control by means of the button (3), using a tensioning mechanism.

7. The cryoprobe according to claim 1, characterized in that the functional tip (2) is configured and adjusted to provide control by means of the button (3), using electric actuators.

8. The cryoprobe according to claim 1, characterized in that the functional tip (2) is configured and adjusted to provide control by means of the button (3), using pneumatic actuators.

9. The cryoprobe according to claim 7, characterized in that it has a controller for automatic or semi-automatic control of the movement of the functional tip (2).

10. The cryoprobe according to claim 1, characterized in that it has an elastic element (7) for pressing the functional tip in a direction towards the first tip (1).

11. The cryoprobe according to claim 1, characterized in that the first tip (1) has a system for heating the surface of the first tip (1), for shortening the time of unfreezing the first tip (1) from the frozen tissue.

12. The cryoprobe according to claim 1, characterized in that the temperature measuring system (6) for the tissue comprises a thermocouple and/or a semiconductor sensor.

13. A method for controlling the cryoprobe according to claim 1, characterized in that it comprises the following steps:
a) Placing the previously shaped first tip (1) in the inner part of the tissue;
b) Activation of the system for destroying tissues for a predetermined time needed to destroy tissues of given thickness;
c) Applying the end of the previously shaped movable functional tip (2) to the place where the first tip (1) is destroying the tissues;
d) Measurement of the physical quantities of the tissues being destroyed;
e) Detecting the exceeded critical values of physical quantities which indicate the destruction of tissues;

f) Distancing the end (4) of the functional tip (2) from the place of tissue destruction;

g) Deactivating the system for destroying tissues;

h) Removing the first tip (1) from the inner part of the tissue.

14. The method for controlling the cryoprobe according to claim 13, characterized in that it uses the cryoprobe having a controller for automatic or semi-automatic control of the movement of the functional tip (2), while step f) and/or g) is performed automatically.

\* \* \* \* \*